United States Patent [19]

Cozzi et al.

[11] Patent Number: 4,801,711
[45] Date of Patent: * Jan. 31, 1989

[54] ETHERS OF SUBSTITUTED HYDROXYMETHLYPYRAZINES

[75] Inventors: Paolo Cozzi; Antonio Pillan; Leone Bertone; Pier P. Lovisolo, all of Milan, Italy

[73] Assignee: Farmitalia Carlo Erba S.r.l., Milan, Italy

[ * ] Notice: The portion of the term of this patent subsequent to Sep. 27, 2000 has been disclaimed.

[21] Appl. No.: 65,131

[22] Filed: Jun. 16, 1987

Related U.S. Application Data

[60] Continuation of Ser. No. 479,361, Mar. 28, 1983, abandoned, which is a division of Ser. No. 321,628, Nov. 16, 1981, Pat. No. 4,406,901.

[30] Foreign Application Priority Data

Dec. 9, 1980 [GB] United Kingdom ................ 8039357

[51] Int. Cl.$^4$ .................. C07D 241/12; C07D 241/18
[52] U.S. Cl. ...................................... 544/336; 544/408
[58] Field of Search ................................ 544/336, 408

[56] References Cited

U.S. PATENT DOCUMENTS

| | | | |
|---|---|---|---|
| 3,901,886 | 8/1975 | Schwartz et al. | 260/250 B |
| 3,928,347 | 12/1975 | Schwartz et al. | 260/250 B |
| 3,952,026 | 4/1976 | Winter et al. | 549/429 |
| 4,002,750 | 1/1977 | Ambrogi et al. | 514/255 |
| 4,051,245 | 9/1977 | Ambrogi et al. | 514/255 |
| 4,267,327 | 5/1981 | Cozzi et al. | 544/336 |
| 4,406,901 | 9/1983 | Cozzi et al. | 514/255 |

FOREIGN PATENT DOCUMENTS 2004186 11/1969 France .

OTHER PUBLICATIONS

Burger, Alfred, *Medicinal Chemistry III* (part I), Wiley-Interscience, New York (1971), pp. 52–53.
Ariens, J. E., *Drug Design*, Academic Press, New York (1971), pp. 10, 80, 81.

*Primary Examiner*—Donald G. Daus
*Assistant Examiner*—W. Teoli
*Attorney, Agent, or Firm*—Armstrong, Nikaido, Marmelstein & Kubovcik

[57] ABSTRACT

Alkoxy methyl pyrazine N-oxides having anti lypolytic, hypotriglyceridemic and hypocholesterolaemic properties and utility are disclosed.

4 Claims, No Drawings

ETHERS OF SUBSTITUTED HYDROXYMETHLYPYRAZINES

This application is a continuation of Ser. No. 479,361, filed Mar. 28, 1983, now abandoned, which is a Rule 60 Divisional of Ser. No. 321,628, filed Nov. 16, 1981, now U.S. Pat. No. 4,406,901, issued Sept. 27, 1983.

DESCRIPTION

The present invention relates to ethers of substituted hydroxymethylpyrazine derivatives, to a process for their preparation and to pharmaceutical compositions containing them.

The compounds of the invention have the following general formula (I)

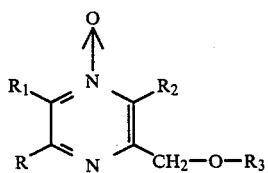

wherein:
each of the groups R, $R_1$ and $R_2$, which may be the same or different, represents a hydrogen atom, a $C_1$-$C_6$ alkoxy or $C_1$-$C_6$ alkyl group, and
$R_3$ represents a straight or branched chain, saturated or unsaturated, $C_1$-$C_8$ aliphatic hydrocarbon group.

Also the possible isomers of the compounds of formula (I), their mixtures and the metabolites and the metabolic precursors and bioprecursors of the compounds of formula (I) are included in the scope of the present invention. The alkyl and alkoxy groups may be branched or straight chain groups.

When one of R, $R_1$ and $R_2$ is $C_1$-$C_6$ alkoxy, it is preferably $C_1$-$C_4$ alkoxy, in particular methoxy or ethoxy.

When one of R, $R_1$ and $R_2$ is $C_1$-$C_6$ alkyl, it is preferably $C_1$-$C_3$ alkyl and more preferably methyl. $R_3$ is preferably a branched or straight chain saturated $C_1$-$C_8$ aliphatic hydrocarbon group, in particular $C_1$-$C_6$ alkyl, preferably methyl or ethyl.

A preferred class of compounds is that represented by the compounds of formula (I), wherein R and $R_2$ are both hydrogen, $R_1$ is $C_1$-$C_6$ alkyl and $R_3$ is $C_1$-$C_6$ alkyl.

More preferred compounds of the invention are the compounds of formula (I) wherein R and $R_2$ are both hydrogen, $R_1$ is $C_1$-$C_3$ alkyl and $R_3$ is $C_1$-$C_4$ alkyl; and more particularly the compounds of formula (I), wherein R and $R_2$ are both hydrogen, $R_1$ is methyl and $R_3$ is methyl or ethyl.

Examples of particularly preferred compounds of the invention are:
2-methoxymethyl-5-methylpyrazine-4-oxide;
2-ethoxymethyl-5-methylpyrazine-4-oxide;
2-n-propyloxymethyl-5-methylpyrazine-4-oxide;
2-i-propyloxymethyl-5-methylpyrazine-4-oxide;
2-n-butyloxymethyl-5-methylpyrazine-4-oxide;
2-tert-butyloxymethyl-5-methylpyrazine-4-oxide;
2-n-pentyloxymethyl-5-methylpyrazine-4-oxide;
2-n-hexyloxymethyl-5-methylpyrazine-4-oxide.

The compounds of the invention may be prepared by a process comprising:
(a) reacting a compound of formula (II)

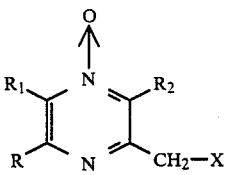

with a compound of formula (III)

$$Y-R_3 \quad \text{(III)}$$

wherein in the above formulae (II) and (III) R, $R_1$, $R_2$ and $R_3$ are as defined above, and one of the groups X and Y is halogen or the residue of a reactive ester of an alcohol and the other is a group —OM, wherein M is hydrogen or a cation, or
(b) oxidizing a compound of formula (IV)

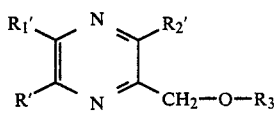

wherein:
each of R', $R'_1$ and $R'_2$, being the same or different, is hydrogen or methyl and $R_3$ is as defined above, so obtaining a compound of formula (I), wherein each of R, $R_1$ and $R_2$, being the same or different, is hydrogen or methyl and $R_3$ is as defined above; and, if desired, transforming a compound of formula (I) so produced into another compound of formula (I) and/or, if desired, separating a mixture of isomers of compounds of formula (I) into the single isomers.

When one of X and Y is halogen, it is preferably chlorine or bromine.

When one of X and Y is the residue of a reactive ester of an alcohol, it is preferably —O-mesyl or —O-tosyl.

When one of X and Y is a group —OM, M is preferably a cation, preferably an alkali metal cation, for example sodium or potassium.

Thus, when X is halogen or the residue of a reactive ester of an alcohol, the compound of formula (II) is reacted with a compound of formula (III) wherein Y is a group —OM; while, when X represents a group —OM, the compound of formula (II) is reacted with a compound of formula (III) wherein Y is halogen or the residue of a reactive ester of an alcohol. The reaction between a compound of formula (II) and a compound of formula (III) may be carried out, for example by using equimolar amounts of the reagents in a solvent such as an aromatic hydrocarbon, preferably benzene, toluene or xylene; or dimethylformamide, dimethylacetamide, hexamethylphosphortriamide, tetrahydrofuran, dioxane or 1,2-dimethoxy-ethane, at temperatures generally from about 20° C. to the reflux temperature of the solvent used, with reaction times generally from about 1 hour to roughly 12 hours. The oxidation of a compound of formula (IV) may, for example, be carried out through organic peracids, e.g; peracetic acid, permaleic acid, monoperphthalic acid or m-chloroperbenzoic acid, prepared in situ by reaction of hydrogen peroxide, for example 30–36% w/v hydrogen peroxide, with the corresponding acid, at temperatures ranging from about 20° C. to the reflux temperature of the reacting mixture, for reaction times ranging from about 1 hour up to about 12 hours. As stated above a compound of formula (I) may be converted, if desired, into another compound of formula (I); this optional process may be carried out by methods known in themselves.

Also the optional separation of a mixture of isomers into the single isomers may be carried out by conventional methods.

Compounds of formula (III) are known in the literature. Compounds of formula (II), in which X is a hydroxy group may be obtained by reduction of compounds of formula (V)

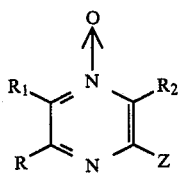

wherein:

R, $R_1$ and $R_2$ are as defined above and Z represents a free, salified or esterified carboxy group.

When, in a compound of formula (V), Z is a salified carboxy group, the salt may be either a salt of an organic base or a salt of an inorganic base; preferably it is an alkali metal salt.

When, in a compound of formula (V), Z is an esterified carboxy group, the ester may be, for example, an alkyl ester; preferably it is a $C_1$–$C_6$ alkoxycarbonyl group, in particular methoxy- or ethoxy-carbonyl.

The reduction of a compound of formula (V), wherein Z is esterified carboxyl, to give a compound of formula (II) wherein X is OH, may, for example, be carried out using sodium borohydride as reducing agent in a solvent such as methanol, ethanol or isopropanol or a mixture of one of these solvents with water in ratios which vary depending on the solubility of the starting product; the said reduction may also be performed e.g. using lithium aluminium hydride in inert solvents such as anhydrous diethyl ether or anhydrous tetrahydrofuran at temperatures which, in both cases, range from approximately 0° C. to the solvent reflux temperature, for reaction times of between approximately 30 minutes and approximately 24 hours.

The reduction of a compound of formula (V) wherein Z represents a free carboxyl group, to give a compound of formula (II), wherein X is OH, is preferably carried out using lithium aluminium hydride in inert solvents such as anhydrous ethyl ether, anhydrous diethylene glycol dimethyl ether, anhydrous tetrahydrofuran or mixtures thereof, or using preformed solutions of boron hydride in the aforesaid anhydrous solvents, or boron hydride prepared in situ in the reaction medium from sodium boronhydride and boron trifluoride etherate, preferably in diethylene glycol dimethyl ether, at temperatures ranging from about 0° C. to the solvent reflux temperature, for reaction times of between approximately 30 minutes and 12 hours.

The reduction of a compound of formula (V) wherein Z represents a salified carboxy group, to give a compound of formula (II) wherein X is OH, is preferably carried out in conditions analogous to those employed in the reduction of a compound of formula (V) wherein Z is a free carboxy group.

The compounds of formula (II) wherein X is —OM, wherein M is a cation, e.g., an alkali metal cation, may be obtained from the corresponding compounds of formula (II) wherein X is —OH, by treatment with a strong appropriate base, e.g. sodium amide or potassium amide, or by treatment with the hydride of an alkali metal, preferably sodium hydride, in the conditions generally used in organic chemistry for this type of salification.

The compounds of formula (II) wherein X is halogen may be obtained from the corresponding compounds of formula (II) wherein X is —OH by known methods, e.g. by treatment with $SOCl_2$ by conventional methods of organic chemistry, optionally in the presence of a suitable catalyst, for example $ZnCl_2$, or by treatment with $SOCl_2$ or oxalic acid dichloride in dimethylformamide, through the formation of a Vilsmeier reagent.

The compounds of formula (II) wherein X is the residue of a reactive ester of an alcohol, e.g. an —O-mesyl or —O-tosyl group, may be prepared from the corresponding compounds of formula (II) wherein X is —OH by known methods, for example by treatment with the suitable acyl halide, preferably chloride, for example with p-toluenesulphonylchloride or methanesulphonylchloride operating, for instance, in anhydrous pyridine at room temperature.

The compounds of formula (IV) are known [for example they are described in J. Org. Chem. 26 (3), 2356, (1960)] or may be prepared by known methods from known compounds, for example, as described in the above reference.

Also the compounds of formula (V) are known [for example, they are described in European Journal Medicine Chemistry-Chimica Therapeutica: 15, 157, (1980)] or may be prepared by known methods, for example, as described in the above reference.

The compounds of the invention possess an elevated lipid-lowering activity, in particular an anti-lipolytic activity (decrease of plasma free fatty acids), triglyceride-, cholesterol- and plasma phospholipid- lowering activity. The above activities of the compounds of the invention were evaluated, on groups of five, six or twelve male OFA-Ico: SD (IOPS Caw) rats, of average weight 180 g, fasted for 18 hours, with water ad libitum.

The compounds to be tested were suspended in Methocel ® (0.5% in distilled water) and administered by stomach tube and in doses ranging from 1 to 50 mg/Kg body weight, each in a volume of 0.5 ml per 100 g of body weight.

The animals were killed at times ranging from the $1^{st}$ to the $7^{th}$ hour after treatment.

Groups of animals treated with the suspending agent only (control groups) were available for each sampling time.

At the times indicated, treated and control animals were slaughtered and blood collected.

The plasma obtained by centrifugation of the blood samples, with addition of 1% heparin in saline (0.1 ml for 5 ml of blood), was assayed for the following variables:

(a) Free fatty acids: by the method of Dole modified by Trout: Dole V.P.—Clin. Invest., 35, 150, (1956); Trout D.L.—J. Lip. Res., 1, 199, (1960)).

(b) Triglycerides: by the method of Mendez: Mendez J.—Clin. Chem., 21, N. 6, 768, (1975).

(c) Total cholesterol: by the method of Allain: Allain C. et al.—Clin. Chem., 20, 470, (1974)).

(d) Phospholipids: by the method of Takayama: Takayama M.—Clin. Chim. Acta, 79, 93, (1977).

In particular, the antilipolytic activity for the compound 2-methoxymethyl-5-methylpyrazine-4-oxide, coded FCE 21990, was studied in comparison with the compound 2-hydroxymethyl-5-methylpyrazine-4-oxide, coded K 10603, which is the most active compound among those described in U.S. Pat. No. 4,267,327; (Table 1).

The said activity was determined according to the methods described above.

For this study one hundred and eight OFA-Ico: SD (IOPS Caw) male rats were used.

The two compounds were administered orally at a single dose of 50 mg/Kg per os.

Blood samples were colleced from the animals at 120 minutes, 180 minutes, 300 minutes, 360 minutes after the single administration. Six animals were sacrificed for each treatment at the sampling times 120 minutes and 180 minutes and twelve animals at the sampling times 300 and 360 minutes. Determination of free fatty acids (FFA) was made, on the plasma samples.

The FFA values for each time and treament were statistically analyzed as follows: mean and standard error calculation, variance analysis: Winner, B. J. "Statistical Principles in experimental design"—Hill Book Company (London, San Francisco, Toronto, New York—1962, Pag. 56–62) with a completely randomized experimental design, and finally by the Dunnett's test: Biometrics, 20, 482, (1964) for each comparison of the control group versus the two treated groups; (Table 2).

For the sake of brevity, the analysis of variance data are not here reported.

At times 120' and 180' after administration the mean FFA values for the groups of rats administered FCE 21990 and K 10603 were shown by Dunnett's test to differ in a highly significant manner ($p \leq 0.01$) from the corresponding values for the control group, the former being lower than the latter.

At time 300', the means of the values for the two treated groups again both differed from the corresponding control group mean, the former being lower than the latter. Such difference is significant ($p \leq 0.05$) for the group administered K 10603, and highly significant ($p \leq 0.01$) for the group treated with FCE 21990.

At time 360', the mean for the group administered FCE 21990 again differed in a highly significant manner ($p \leq 0.01$) from the mean of the control group, the former being lower than the latter.

The mean of the group administered K 10603 did not differ from the mean of the control group. It can therefore be concluded that the antilipolytic activity of the compound FCE 21990 remains high up to the time 360': in fact, at this sampling time the mean of the FFA levels of the animals treated with this compound is lower than that of the control animals, with a significance level of $p \leq 0.01$.

The antilipolytic activity of the compound K 10603 is shorter-lasting: at time 300' the means of the FFA values after administration of this compound is lower than the mean of the controls, with a significance level $p \leq 0.05$.

At time 360' the mean of the FFA values after administration of K 10603 does not differ from that of the control animals, meaning that the antilipolytic effect has ceased.

As it is of very great importance in therapy with antilipolytic agents that their activity be protracted over time as long as possible, the foregoing experimental data clearly demonstrate the progress made with the compound FCE 21990.

TABLE 1

Plasma levels of free fatty acids (FFA, espressed as μmoles %) in rats at various times (in minutes) after treatment

| Treatment | Dose mg/Kg per os | FFA μmoles % 120' | 180' | Means ± S.E. 300' | 360' |
|---|---|---|---|---|---|
| Controls* | — | 57.5 + 5.9 | 62.8 + 4.4 | 66.6 + 3.2 | 71.7 ± 5.2 |
| FCE 21990 | 50 | 15.0 ± 2.3 | 17.8 ± 1.1 | 39.3 ± 3.6 | 39.2 ± 5.2 |
| K 10603 | 50 | 13.7 ± 1.2 | 17.7 ± 2.6 | 50.9 ± 6.2 | 77.5 ± 6.9 |
|  |  | n = 6 | n = 6 | n = 12 | n = 12 |

*Methocel 0.5% in distilled water, 5 ml/Kg per os
n = number of animals for each treatment

TABLE 2

Results of Dunnett's test on the values of FFA reported in Table 1

| Sampling time in minutes | Comparisons | | Result |
|---|---|---|---|
| 120' | Controls → FCE 21990 | 50 mg/Kg per os | HS |
|  | Controls → K 10603 | 50 mg/Kg per os | HS |
| 180' | Controls → FCE 21990 | 50 mg/Kg per os | HS |
|  | Controls → K 10603 | 50 mg/Kg per os | HS |
| 300' | Controls → FCE 21990 | 50 mg/Kg per os | HS |
|  | Controls → K 10603 | 50 mg/Kg per os | S |
| 360' | Controls → FCE 21990 | 50 mg/Kg per os | HS |
|  | Controls → K 10603 | 50 mg/Kg per os | NS |

NS = not significant ($p > 0.05$)
S = significant ($p \leq 0.05$)
HS = highly significant ($p \leq 0.01$)

In view of their high lipid-lowering activity, these new compounds are useful in the therapy of primary and secondary hyperlipidaemias.

In particular, because of their antilipolytic activity they can reduce the incidence of ventricular arrhythmias in infarct patients (Rowe H.J., 1975, LANCET 1, 295).

They may be administered in a variety of dosage forms, e.g. orally in the form of tablets, capsules, sugar- or film-coated tablets, liquid solutions or suspensions; rectally, in the form of suppositories; parenterally, e.g. intramuscularly or by intravenous injection or infusion.

The dosage depends of the age, weight, conditions of the patient and administration route; for example the dosage adopted for oral administration in adults ranges from about 50 to about 150 mg pro dose, from 1 to 3 times daily, preferably from 50 to 100 mg pro dose 1–3 times a day.

The toxicity of the compounds of the invention was found to be quite negligible and therefore they can be safely used in therapy. The evaluation of the toxicity (as orientative acute toxicity, i.e. $LD_{50}$), was carried out, e.g., as follows: nine hours food-deprived mice were treated orally with single administration of increasing doses, then housed and normally fed; the $LD_{50}$ was assessed on the seventh day after treatment.

For example, the following data were obtained:

2-methoxymethyl-5-methylpyrazine-4-oxide:
  LD$_{50}$>800 mg/Kg
2-ethoxymethyl-5-methylpyrazine-4-oxide: LD$_{50}$>800 mg/Kg.

The scope of this invention includes also pharmaceutical compositions comprising a compound of formula (I) which may, if desired, be in any isomeric form, in association with a pharmaceutically acceptable excipient (which can be a carrier or diluent).

The pharmaceutical compositions containing the compounds of the invention are usually prepared by conventional methods and administered in a pharmaceutically suitable form.

For example, the solid oral forms may contain, together with the active compound, diluents, e.g., lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethyl cellulose or polyvinyl pyrrolidone; disaggregating agents, e.g. a starch, alginic acid, alginates or sodium starch glycolate; effervescing mixtures; dyestuffs; sweeteners; wetting agents, such as, lecithin, polysorbates or laurylsulphates; and in general, non-toxic and pharmacologically inactive substances generally used in pharmaceutical formulations. Said pharmaceutical preparations may be manufactured in known manner, for example, by means of mixing, granulating, tabletting, sugar-coating, or film-coating processes. The liquid dispersions for oral administration may be e.g. solutions, syrups, emulsions or suspensions. The solutions for oral administration may contain as carrier, for example, water with a suitable amount of a dyestuff and/or sweeteners agents. The syrups may contain as carrier, for example, saccharose or saccharose with glycerine and/or mannitol and/or sorbitol; in particular, a syrup to be administered to diabetic patients can contain as carriers only products not metabolizable to glucose, or metabolizable in only very small amounts to glucose, such as sorbitol.

The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain together with the active compound a pharmaceutically acceptable carrier, e.g. sterile water, olive oil, ethyl oleate, glycols, e.g. propylene glycol, and if desired, a suitable amount of lidocaine hydrochloride.

The solutions for intravenous injections or infusions may contain as carrier, for example, sterile water or preferably they may be in the form of sterile, aqueous, isotonic saline solutions.

The suppositories may contain, together with the active compound, a pharmaceutically acceptable carrier, e.g. cocoabutter, polyethylene glycol, a polyoxyethylene sorbitan fatty acid ester surfactant or lecithin.

The following Examples serve to illustrate the invention. The I.R. spectrum of the compounds was measured in solid phase (KBr) or in Nujol solution or in a solution of a suitable solvent such as CHCl$_3$, using a Perkin-Elmer 125 spectrophotometer.

The N.M.R. Spectrum was measured preferably in solution of dimethyl sulphoxide-d$_6$ or of CDCl$_3$, using a 90 M-hertz Bruker HFX apparatus.

The R$_f$ Values were determined by thin layer chromatography on ready-to-use silica gel plates of 0.25 mm coating thickness.

EXAMPLE 1

A solution of 2-hydroxymethyl-5-methylpyrazine-4-oxide (2.1 g) in anhydrous dimethylformamide (10 ml) was treated with a suspension of sodium hydride (0.4 g) in anhydrous dimethylformamide (5 ml).

The reaction mixture was stirred at room temperature until the hydrogen production was ceased, then a solution of methyl iodide (2.5 g) in anhydrous dimethylformamide (10 ml) was added portionwise.

After two hours stirring at room temperature, the reaction mixture was evaporated to dryness under vacuum and the residue was taken up with water (50 ml) and repeatedly extracted with diethyl ether. The organic phase was washed with water, dried and evaporated to dryness. The residue, treated with n-pentane, gave 2-methoxymethyl-5-methylpyrazine-4-oxide, (1.6 g) as white solid, m.p. 69°-72° C.

Analysis:
Found:  C 53.92; H 6.52; N 17.92
calculated for C$_7$H$_{10}$N$_2$O$_2$: C 54.53; H 6.54; N 18.17
T.L.C. (diethylether: methanol = 180:20) R$_f$ = 0,31
I.R. (CHCl$_3$)  ν3120 cm$^{-1}$  (C—H aromatics)
  ν3080 cm$^{-1}$
  ν2940 cm$^{-1}$  (C—H aliphatics)
  ν2900 cm$^{-1}$
  ν2830 cm$^{-1}$
  ν1600 cm$^{-1}$  (C=C, C=N)
  ν1520 cm$^{-1}$
  ν1310 cm$^{-1}$  (N⟶O)
N.M.R. (CDCl$_3$): δppm  2.48 (s; 3H; C$\underline{H}_3$—C=)
  3.52 (s; 3H; —O—C$\underline{H}_3$)
  4.58 (s; 2H; —C$\underline{H}_2$—O—CH$_3$)

8.32 (s; 1H; =N—C$\underline{H}$=)

8.44 (s; 1H; —C$\underline{H}$=N—)

The following compounds were similarly obtained:
2-ethoxymethyl-5-methylpyrazine-4-oxide (semi-solid oil)

Analysis:
Found:  C 56.54; H 7.06; N 16.21
Calculated for C$_8$H$_{12}$N$_2$O$_2$:  C 57.13; H 7.19; N 16.65
T.L.C.: (diethylether: methanol = 180:20) R$_f$ ≈ 0.4
N.M.R. (CDCl$_3$): δp.p.m.  1.27 (t; 3H; —CH$_2$—C$\underline{H}_3$)

2.47 (s large; 3H; C$\underline{H}_3$—C=)

3.65 (q; 2H; —C$\underline{H}_2$—CH$_3$)

4.60 (s large; 2H; =C—C$\underline{H}$—O—)

8.28 (s large: 1H; =N—C$\underline{H}$=)

8.40 (s large; 1H; —C$\underline{H}$=N—)
I.R. (CHCl$_3$):  ν2930 cm$^{-1}$  (C—H aliphatics)
  ν2870 cm$^{-1}$ -continued

| | |
|---|---|
| ν1600 cm⁻¹ | (C=C, C=N) |
| ν1515 cm⁻¹ | |
| ν1305 cm⁻¹ | (N——>O) |
| ν1110 cm⁻¹ | (C—O—C) |

2-ethoxymethyl-5-n-propylpyrazine-4-oxide (semi-solid oil)

| Analysis: | | | | | | |
|---|---|---|---|---|---|---|
| Found: | C | 60.59; | H | 8.07; | N | 14.11 |
| Calculated for $C_{10}H_{16}N_2O_2$: | C | 61.20; | H | 8.21; | N | 14.27 |
| I.R. (CHCl₃): | δ 2940 cm⁻¹ | | (C—H aliphatics) | | | |
| | δ 2900 cm⁻¹ | | | | | |
| | δ 2830 cm⁻¹ | | | | | |
| | δ 1600 cm⁻¹ | | (C=C; C=N) | | | |
| | δ 1515 cm⁻¹ | | | | | |
| | δ 1305 cm⁻¹ | | (N → O) | | | |

2-n-propyloxymethyl-5-methylpyrazine-4-oxide;
2-i-propyloxymethyl-5-methylpyrazine-4-oxide;
2-n-butyloxymethyl-5-methylpyrazine-4-oxide;
2-tert-butyloxymethyl-5-methylpyrazine-4-oxide;
2-n-pentyloxymethyl-5-methylpyrazine-4-oxide; and
2-n-hexyloxymethyl-5-methylpyrazine-4-oxide.

EXAMPLE 2

2-Hydroxymethyl-5-methylpyrazine-4-oxide (3.5 g) was dissolved under stirring in a solution of 8 ml of thionyl chloride in 20 ml of dry benzene containing 0.5 g of ZnCl₂, keeping the temperature below 30° C. The reaction mixture was cautiously warmed 3 hours at 60° C., then cooled to room temperature, and filtered. The solvent was evaporated under reduced pressure. The oily residue was dissolved in a solution of sodium methoxide in methyl alcohol, previously prepared dissolving 0.6 of sodium in 30 ml of methyl alcohol. After refluxing 4 hours, the reaction solution was cooled at room temperature, filtered and evaporated to dryness. The residue was taken up with water and repeatedly extracted with ethyl ether. The organic phase was washed with water, dried and the solvent was evaporated to dryness; the residue treated with pentane gave 2-methoxymethyl-5-methylpyrazine-4-oxide (1.5 g), m.p. 69°-72° C.

The following compounds where similarly obtained:
2-ethoxymethyl-5-n-propylpyrazine-4-oxide;
2-ethoxymethyl-5-methylpyrazine-4-oxide;
2-n-propyloxymethyl-5-methylpyrazine-4-oxide;
2-i-propyloxymethyl-5-methylpyrazine-4-oxide;
2-n-butyloxymethyl-5-methylpyrazine-4-oxide;
2-tert-butyloxymethyl-5-methylpyrazine-4-oxide;
2-n-pentyloxymethyl-5-methylpyrazine-4-oxide; and
2-n-hexyloxymethyl-5-methylpyrazine-4-oxide.

EXAMPLE 3

2-ethoxymethyl-5-methylpyrazine [J.O.C. 26 (3), 2356, (1960)] (1.0 gr) was heated with 36% w/v hydrogen peroxide (0.7 ml) in glacial acetic acid (2.15 ml) for 5 hours at 60° C., then 0.7 ml of 36% w/v hydrogen peroxide were added and the reaction mixture was heated for 5 hours.

The solution was concentrated under reduced pressure to about one third of the starting volume and diluted with an equal amount of cold water. The solution was made alkaline with 20% sodium hydroxide and extracted with chloroform.

The combined extracts were dried, the solvent stripped under reduced pressure and the residue was purified by column chromathography on eluting with $C_2H_5OH: CH_3OH = 190:5$ to give 2-ethoxymethyl-5-methylpyrazine-4-oxide (semi-solid oil).

| Analysis: | | | | | | |
|---|---|---|---|---|---|---|
| Found: | C | 56.80; | H | 6.95; | N | 16.35 |
| Calculated for $C_8H_{12}N_2O_2$: | C | 57.13; | H | 7.19; | N | 16.65 |

The following compound where similarly obtained:
2-methoxymethyl-5-methylpyrazine-4-oxide;
2-n-propyloxymethyl-5-methylpyrazine-4-oxide;
2-i-propyloxymethyl-5-methylpyrazine-4-oxide;
2-n-butyloxymethyl-5-methypyrazine-4-oxide;
2-tert-butyloxymethyl-5-methylpyrazine-4-oxide;
2-n-pentyloxymethyl-5-methylpyrazine-4-oxide; and
2-n-hexyloxymethyl-5-methylpyrazine-4-oxide.

The starting materials for use in Examples 1 and 2 may be prepared in accordance with the following Examples 4 and 5.

EXAMPLE 4

To a solution of 2-carbomethoxy-5-methylpyrazine-4-oxide (6.3 g) in a mixture of water (50 ml) and methyl alcohol (25 ml) cooled to a temperature between 0° C. and 5° C., sodium boronhydride (4.25 g) was added in portions, under stirring and maintaining the temperature below 10° C. The reaction mixture was stirred for 2 hours at room temperature, the solvent then evaporated under vacuum and the residue extracted several times with methanol under heating. After evaporation to dryness, the residue was taken up with CHCl₃ and filtered.

By first dehydrating the chloroform extracts and then evaporating to dryness, 4 g (76%) of 2-hydroxymethyl-5-methylpyrazine-4-oxide, m.p. 110°-111° C., were obtained.

| Analysis: | | | | | | |
|---|---|---|---|---|---|---|
| Found: | C, | 51.37: | H, | 5.76; | N, | 19.94 |
| Calculated for $C_6H_8N_2O_2$: | C, | 51.42; | H, | 5.75; | N, | 19.99 |
| T.L.C.: mobile phase: CHCl₃:CH₃OH = 170:30 | | | | | | |
| R_f = 0.38 | | | | | | |
| N.M.R. (CDCl₃) δ ppm | (2.42 3H s) | | | | | |
| | (4.36 1H broad band) | | | | | |
| | (4.74 2H s) | | | | | |
| | (8.3 1H s) | | | | | |
| | (8.38 1H s) | | | | | |

The 2-carbomethoxy-5-methylpyrazine-4-oxide used as starting material was prepared, with a yield of 83% from 2-carboxy-5-methylpyrazine-4-oxide refluxed for twelve hours in anhydrous methanol in the presence of boron trifluoride etherate, m.p. 146°-148° C.

| Analysis: | | | | | | |
|---|---|---|---|---|---|---|
| Found: | C, | 49.91; | H, | 4.82; | N, | 16.58 |
| Calculated for $C_7H_8N_2O_3$: | C, | 50.00; | H, | 4.80; | N, | 16.65 |
| T.L.C. mobile phase: CHCl₃:CH₃OH:NH₂OH = 190:10:0.5 | | | | | | |
| R_f = 0.61 | | | | | | |

EXAMPLE 5

To a solution of 2-carboxy-5-methylpyrazine-4-oxide (1.5 g) in diethylene glycol dimethyl ether (80 ml), a (1M) solution of diborane in tetrahydrofuran (30 ml) was added at 0° C. under an atmosphere of nitrogen. To the reaction mixture, maintained for 3 hours at 0° C. and 1 hour at room temperature, was cautiously added ethanol (50 ml) and then a 0.5M solution of alchoholic KOH (25 ml). The resultant solution, after evaporation at reduced pressure, was taken up with chloroform so obtaining, after evaporation to dryness, 1.2 g of 2-hydroxymethyl-5-methylpyrazine-4-oxide.

FORMULATION EXAMPLES

Formulation I: Tablet

Tablets, each weighing 300 mg and containing 100 mg of the active substance are manufactured as follows:

| Composition (for 10,000 tablets) | |
|---|---|
| 2-Methoxymethyl-5-methylpyrazine-4-oxide | 1000 g |
| Lactose | 1420 g |
| Corn starch | 475 g |
| Talc powder | 75 g |
| Magnesium stearate | 30 g |

2-methoxymethyl-5-methylpyrazine-4-oxide, lactose, and half of the corn starch are mixed; the mixture is then forced through a sieve of 0.5 mm openings. Corn starch (18 g) is suspended in warm water (180 ml). The resulting paste is used to granulate the powder. The granules are dried, comminuted on a sieve of sieve size 1.4 mm, then the remaining quantity of starch, talc and magnesium stearate is added, carefully mixed, and processed into tablets using punches of 10 mm diameter.

Formulation II: intramuscular injection solution

An injectable pharmaceutical composition was manufactured by dissolving 50-100 mg of 2-methoxymethyl-5-methylpyrazine-4-oxide in sterile water or sterile aqueous normal saline solution (1-2 ml).

Formulation III: Capsule

By the usual pharmaceutical techniques, capsules having the following composition were prepared:

| 2-Methoxymethyl-5-methylpyrazine-4-oxide | 50 mg |
|---|---|
| Lactose | 298 mg |
| Corn Starch | 50 mg |
| Magnesium stearate | 2 mg |

Formulation IV: Suppository

By the usual pharmaceutical techniques, suppositories having the following composition were prepared:

| 2-Methoxymethyl-5-methylpyrazine-4-oxide | 0.05 g |
|---|---|
| Lecithin | 0.07 g |
| Cacao butter | 0.88 g |

We claim:

1. A compound of the formula

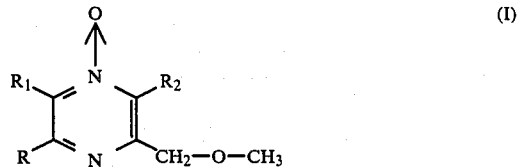

wherein each of the groups R, $R_1$ and $R_2$, which may be the same or different, is a hydrogen atom or a $C_1$–$C_6$ straight or branched chain alkoxy or $C_1$–$C_6$ straight or branched chain alkyl group.

2. Compound of claim 1, wherein R and $R_2$ are both hydrogen and $R_1$ is alkyl.

3. Compound of claim 2, wherein $R_1$ is a $C_1$–$C_3$ straight or branched chain alkyl group.

4. 2-Methoxymethyl-5-methylpyrazine-4-oxide.

* * * * *